United States Patent
Castex-Rizzi et al.

(10) Patent No.: US 11,857,578 B2
(45) Date of Patent: *Jan. 2, 2024

(54) EXTRACT AND DERMATOLOGICAL COMPOSITION COMPRISING SAME, FOR TREATING SENSITIVE SKIN

(71) Applicant: PIERRE FABRE DERMO-COSMETIQUE, Boulogne-Billancourt (FR)

(72) Inventors: Nathalie Castex-Rizzi, Colomiers (FR); Bertrand Chol, Villy le Pelloux (FR); Fabrice Lestienne, Vernet (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/059,810

(22) PCT Filed: May 31, 2019

(86) PCT No.: PCT/EP2019/064211
§ 371 (c)(1),
(2) Date: Nov. 30, 2020

(87) PCT Pub. No.: WO2019/229248
PCT Pub. Date: Dec. 5, 2019

(65) Prior Publication Data
US 2021/0353690 A1    Nov. 18, 2021

(30) Foreign Application Priority Data
Jun. 1, 2018    (FR) ..................... 1854794

(51) Int. Cl.
*A61K 35/741* (2015.01)
*A61P 29/00* (2006.01)

(52) U.S. Cl.
CPC ............ *A61K 35/741* (2013.01); *A61P 29/00* (2018.01)

(58) Field of Classification Search
None
See application file for complete search history.

(56) References Cited

U.S. PATENT DOCUMENTS 11,484,555 B2 * 11/2022 Castex-Rizzi ......... A61K 33/34
2018/0125951 A1    5/2018 Hsia et al.
2020/0030387 A1 * 1/2020 Castex-Rizzi ........... C12N 1/20

FOREIGN PATENT DOCUMENTS

EP          2018891 A1    1/2009
RU          2615140 C2 *  4/2017    .............. A61P 37/02
WO    WO 2012/085182 A1  6/2012

OTHER PUBLICATIONS

RU2615140C2 translated doc (Year: 2017).*
Chen et al., "Brain-Skin Connection: Stress, Inflammation and Skin Aging," Inflammation & Allergy—Drug Targets, vol. 13, No. 3, 2014, pp. 177-190.
International Search Report (PCT/ISA/210) for International Application No. PCT/EP2019/064211, dated Sep. 16, 2019.
Misery et al., "Neuropathic pruritus," Nat. Rev. Neurol., vol. 10, 2014 (published online Jun. 10, 2014), pp. 408-416.
Needleman et al., "A General Method Applicable to the Search for Similarities in the Amino Acid Sequence of Two Proteins," J. Mol. Biol., vol. 48, 1970, pp. 443-453.
Pearson et al., "Improved tools for biological sequence comparison," Proc. Natl. Acad. Sci. USA, vol. 85, Apr. 1988, pp. 2444-2448.
Smith, "Comparison of Biosequences," Advances in Applied Mathematics, vol. 2, 1981, pp. 482-489.
Tatusova et al., "Blast 2 Sequences, a new tool for comparing protein and nucleotide sequences," FEMS Microbiology Letters, vol. 174, 1999, pp. 247-250.

* cited by examiner

Primary Examiner — Terry A McKelvey
Assistant Examiner — Jacob A Boeckelman
(74) Attorney, Agent, or Firm — Birch, Stewart, Kolasch & Birch, LLP

(57) ABSTRACT

The invention relates to a new bacterial extract that can be used for protecting and/or treating sensitive skin and/or reactive, intolerant skin, particularly by means of targeted action on neurogenic inflammation of the skin. The invention also relates to cosmetic or dermatological compositions comprising such a bacterial extract as an active ingredient.

9 Claims, No Drawings

Specification includes a Sequence Listing.

SEQUENCE LISTING

<160> NUMBER OF SEQ ID NOS: 2

<210> SEQ ID NO 1
<211> LENGTH: 1487
<212> TYPE: DNA
<213> ORGANISM: Artificial Sequence
<220> FEATURE:
<223> OTHER INFORMATION: New bacterium LMB64, class of beta-proteobacteria

<400> SEQUENCE: 1

```
agtttgatca tggctcagat tgaacgcggg cggcatgctt tacacatgca agtcgaacgg      60
cagcacgggc ttcggcctgg tggcgagtgg cgaacgggtg agtaatgcgt cggaacgcgc     120
cgagtagtgg gggataacgc agcgaaagct gtgctaatac cgcatacgta ctgaggtaga     180
aagtggggga ccttcgggcc tcacgctatt cgagcggccg acgtctgatt agctagttgg     240
tggggtaaag gccccaccaag cgacgatca gtagcgggtc tgagaggatg atccgccaca     300
ctgggactga gacacggccc agactcctac gggaggcagc agtgggaat tttggacaat      360
gggcgcaagc ctgatccagc catgccgcgt gtctgaagaa ggccttcggg ttgtaaagga     420
cttttgtccg ggagcaaagc ctgcttgtta ataccgagtg gggatgagag taccggaaga     480
ataagcaccg gctaactacg tgccagcagc cgcggtaata cgtagggtgc aagcgttaat     540
cggaattact gggcgtaaag cgtgcgcagg cggttgtgca agtctgatgt gaaagccccg     600
ggctcaacct gggaacggca ttggagactg cacggctaga gtgcgtcaga gggggtaga     660
attccacgtg tagcagtgaa atgcgtagag atgtggagga ataccgatgg cgaaggcagc     720
cccctgggat gacactgacg ctcatgcacg aaagcgtggg gagcaaacag gattagatac     780
cctggtagtc cacgccctaa acgatgtcaa ttagctgttg ggggtttgaa tccttggtag     840
cgaagctaac gcgtgaaatt gaccgcctgg ggagtacggc cgcaaggtta aaactcaaag     900
gaattgacgg ggacccgcac aagcggtgga tgatgtggat taattcgatg caacgcgaaa     960
aaccttacct gctcttgaca tgtaccgaag cctgaagaga tttgggtgtg cccgaaaggg    1020
agcggtaaca caggtgctgc atggctgtcg tcagctcgtg tcgtgagatg ttgggttaag    1080
tcccgcaacg agcgcaaccc ttgtcattag ttgccatcat ttggttgggc actctaatga    1140
gactgccggt gacaaaccgg aggaaggtgg ggatgacgtc aagtcctcat ggcccttatg    1200
agcagggctt cacacgtcat acaatggtcg gtacagaggg tcgccaagcc gcgaggtgga    1260
gccaatctca gaaagccgat cgtagtccgg atcgcactct gcaactcgag tgcgtgaagt    1320
cggaatcgct agtaatcgca gatcagcatg ctgcggtgaa tacgttcccg ggtcttgtac    1380
acaccgcccg tcacaccatg ggagtggggg ataccagaag tgggtaggct aaccgcaagg    1440
gaggccgctt accacggtat gcttcatgac tggggtgaag tcgtaac                  1487
```

<210> SEQ ID NO 2
<211> LENGTH: 10948
<212> TYPE: DNA
<213> ORGANISM: Artificial Sequence
<220> FEATURE:
<223> OTHER INFORMATION: New bacterium LMB64, class of beta-
      proteobacteria

<400> SEQUENCE: 2

```
gggcgcagca ccatcgccca ggccaaaagc caccgtgcc gattcggcgg cctgttgctc       60
gcgctcaatg cgctgcgcct ggtcggccaa gtcggcggct tgctgctcgg ccttgcccgc     120
cagggtgtca cgctcgcggg tcagttccgc cacctgctcg gctagggcat cgcgctcggc     180
ctcgatcacc tcaccagcgg ccgccagctc ggcggcttcg ctctgcgcct ggaccaagcg     240
gccctcgacc tcggcgcggg cctgggcggc tgcgcgctcg atctcggcgg caatggcggc     300
ggtcaatgcc tggggcagtt ccgcgcagc agcagcggcc accggccggg cctctcgcca     360
ggcagttaga tgcttgtgaa cggtattcgg gctgccggtg cccaaacgct cgcggatcgc     420
gcggatagtc ggctgctgcc cttcgccgac cagcgcatca gcggcggcgg cgaacgggtg    480
```

-continued

```
gcccgtgcag aggcccgcgt cgagcagatc gagcagcagg ccgccaaggc ggcacaggcc      540
cacgaagaag cccgcgccgc cgccacgcag gaagcccggc aagtgcaagc cgaacgcgac      600
gaagcccgca aggtggccgc cgaggcgcgc gagcagaccg cgcgcctggc tgggcaactc      660
gaagccctca ccgcgaagga gcgaaaagcc gatgaaagac cgtgaccaca acgaagcgat      720
ggccggcatg tttcaggccg accccgatt tgccgccgac tatctgcgcc aggtgttggc      780
cgatggcgag cctaccgacg tgcgcgccgg cttgcggcaa atggcggatg tgctgcgcgt      840
cagtcaggcc gccgcgccga ccgattctgc gccttcggcg ggcctctttg accgggccgg      900
cgtgcgctac gaagtggcgt gcgatgtgat cggggcgttg attgcccatt acgccgaaat      960
catgggacgg gaacgcgagc aggcgcagcc gaatgaggcg gttttgcgcg tggccggagc     1020
catgaaggcg gcgctggccg gggagcggga tgatctcgat ccgcgcgata gcgcggcat      1080 cgaggcggcg atttcgcgct atgcgccact ggcgcgccgg ctgtatggcc aggctgaaaa     1140
cgaccacgcc cgccaggaac agcgtcgcgc cgatttcgac caggtgcatg cttcgctggc     1200
cttggagggg ctggccatga gcgcggacga tttggcggtt caggcgctgc tgatccgggg     1260
cgacattacc cacgatgagg cggtgcagtg ctaccgcatc ctgcatcgcc atgcgcggta     1320
aaaccgactg gccgccgag gtggccggtg tgctgggttt gctcgaatcg cagccgccag     1380
aggcggcgat gctggtgggc tgttttctgg cggcggtagc ccatcccgat catgcggccg     1440
aattggcgat gttcgacaaa ttgccgccag cggcccggat ggtcgtcggg cgattttcc     1500 tcgttttct ggcgggcggc ctggacgatg ccgggcgcga aaaactgcat cgcacatgc     1560 aggcatggtt tgtccgtcag cgccgttttc ggtgaatggc ttgcctcatc cactagggcc     1620
gggcaagggg tgaacagcgg gcgatgctgg cttgcgggac gaccccgcac ccccggaaaa     1680
cttgtcacac accacgcaac tcccgttgct tcgctaaaag ccttgtgccg caaggctttt     1740
agcgaggcga caccgaagac acatcgcggc gacaccgaaa gggccgaacc ggcctaaaac     1800
ccttgctgcg caaggagaac agccgcgctt tcgcgcgcga aagtgcttca aatgcctgtc     1860
ggcatcagca gggtatggat cggcacgccg aaggcgttgg cgatgcgctc caggttgtcc     1920
aaggagatgt ttctgacttg gcgctcgcag tgcgcaacga aggtgcgatg taggccgcac     1980
tcaaaggcga gcgcttcttg tgaccagcct cttttcccgg gtaatcggat catgttggcc     2040
gcgagcacgg cccgcgcgga atgcgcggtt ggtgcgggag gttgagcggc gggagacatg     2100
caaaccagtc tcctgatatg ccgcttttac gtcagccgtg tttaagtcac aatatggttt     2160
tctcatagag aaagacggcg tgacgatggg cagaaaaaca gcaatcaggc gaggggtgc      2220 cgtgttggcc agcctgttga tttgcgcaat tgaaccggtc ggcgcggcct ccctggtcgg     2280
cggtcaaacc gatgattccg tgtgcgacct gggcagcgcg ccacagaacg cccggaagct     2340
gtcggcagcg ggcgacttca tccgcgcgca gtgcaaaaac ggtcaaatgt tggtgggttc     2400
cggcatcgtg cctgccggcg ggtttgactc ggaagtggtg cgcctggcgc gcaccttctg     2460
ccgcatggcg gacattcaga ctcggcgcac gcagggcaac atggccggcc tcgtcatgga     2520
gatcgacgag gtacggtgca tcatcgggaa gttgccgaca tgagaaaagc gatgttggct     2580
ggctttctgg ccgttgtggt ggccaacgtg gttgccgctg agggcggtgc gcccttgcgc     2640
ggcggtgttt gcatcggacc gttccgtggc gctgattccg tcgtgcactg cgagcacatc     2700
ggcaaggtga cgatccgcca gatttacgaa aagggctttc gggtcgttca catgcaggac     2760
gacaagaaca cagccagcta cgttgtgctg gttatcgagg agcaggcgcg atgagggcga     2820
aagcgtggcg gatgctgttt gccgggcggc gctgggtgct ctggcttccc gtgccggcgt     2880
```

```
cggtatggct ggcactgccc gaatggcagc acattcccgc catgttgttg ggcggcctga  2940
tcgtgtggat tcccttctgg ctcgcgtggt ggctcagtga tggcttcgcg ggcatgtcca  3000
ggtggccagg aaccggcgca cctgcggtat ctggcggggt gaacccgcac accggcaagc  3060
catgcacggt gtatcaccag ccgtggggag ataccttcgt gggtggagac tgattatttg  3120
attgaggaac gatgacaagg gccagcaaca agctggccct tgtcgttttc tggactgttt  3180
tacccacaac atccgctctg ctgctgaatt ggcggacatg gcaccgagcc gaacgaacag  3240
aacacgcagc aatccccggg cttggggcgc agcagcgtat ggcaggccgg gcactcgtag  3300
tagaactggc aggcgtccgt gggcatggtt tcctgctgtg cgtggccgca gtgcgggcag  3360
gtcagcacgg attcgagaat gacggcgctc atcgtggcgt acctctgca cggtggacgg  3420 atagcctgcg ttcgtcgttg ccgaggtcaa cgcttccggc ttggccttgt cggcgtcata  3480
ggtgacggtg ccgttttcct tgtcgaaatc gaccttgacg cgctcacac cgggcacttt  3540 ctccagcgac ttcttgactg tgatcgggca tagctcgcag gtcatgttct gaacggccag  3600
cgtgacggtt ttcggggtgg cggccagcac ggcgagcggc acggcagcca gcagagcaat  3660
cagcagtttg cgcatgggag tctccttttca atagaacagc ggggcgaacc acggcacggc  3720
caacagggca agcaacagca cagtgacgat ccagaacgtc aggcgctgcc gctggcgtgt  3780
gcgcggatca gcgcatggcg tgccgggcgt gcagacctgc ggcaccagat agagcttgcg  3840
gaaggccagt ccgagaaaga gcagcgtcat gccgatgaaa aagggccggt acggctccat  3900
cgcggtcagg ctgccaaccc atgagccacc aatgccaagc accagcagga caagcggccc  3960
gacacagcac accgacgcgc cgatggcggt cagtacgctc acgatcaacg agctttttc  4020 agtgagtcgt gccatgtcgc tttccttgta cctgtttgcc caagtgttac tctaaatccc  4080
gtacctaagt acgagtcaa gggggtgtga tgggaacaga actgaccatc ggcaagctgg  4140
ctgacgctgc cggggtgaat atcgagacga ttcgctacta ccagcggcgc ggcctgctgg  4200
atgagccgcc taaccgcca ggggggcatc ggcgctatgc gcctgagcag gcaaaacgtg  4260
tgcgatttat caagcgggca caggcgcttg gtttcacgct ggacgaggta ggcgcgctac  4320
tgaccctgga tgcggcctgc gcctgcgtg agacgcgagc gctggctgtg cgcaagctgg  4380
gtctgatcga gcagaagatg gctgacctcg cggccatgcg gcaggcgctg ggtggattgg  4440
tgcagcagtg tgatgcgggc gacggtggag ccagctgtcc catcatcgac gtgctggcag  4500
gtaattagat gtgttcaaaa aatggtggtt ttctggacac atgccggttt gccctgtcct  4560
gagttgtcct gatgcgttaa agtgttcatt tattcgttca gctttcaatg tggcggaact  4620
gttcatgaat caacgcatcg gctatgcccg cgtttcgacc gacgaccaaa acctagacct  4680
gcaacgggac gcactccggc aggctggatg ctcaaccatt tacgaggaag cagccagcgg  4740
aaagagcgca gcaaggcccg agcttgagca gtgtcggaag gctctccggc ccggcgacac  4800
gcttgtggtg tggcggcttg atcgccttgg gcgcagcctg cccgacctgg tgcagatcgt  4860
ggctgatctt gaacagcgcg gcgtgcattt cgagagcctg accgagaaga tcgagacggg  4920
gagcgcagcg ggtaagctgc aattccatgt tttcgctgca ctcgccgagt tcgagcgcgg  4980
cctgatccgg gagcgaaccc gggcagggct ggatgcagct cgcgcccgtg gccgatccgg  5040
tggacgcaaa ccgaagctgg acgccaagca gatacgccac attaaggcgc tactacgtga  5100
cccgaatacc tgtgttgctg aactcgcccg tgactacggc gtgtcgagaa caactatcta  5160
taaacactgc ggtgtggttc tgccgcgtac agccgatgaa ggggcaatat gacaaaaaag  5220
acaacagcat tcgatgtatt cgagaaatgc gtccaagcag ttcaggctgg tgaactgatc  5280
```

```
gaatccgttt ctgcgaagga caaggaattc catttccaga actggtttca gaagcgcctc    5340
cagagcctgt cgatgcactt cgaggggtcg ggtcgcaaca cctacccgga cttctgcttg    5400
gtagagcaca ccgagggcta cgagatcaag ggtttggcat ggcctggccg cgagcgcgac    5460
tacgactcga acagccaagt gccgactggc tatcacaacg gccgtcaaat cttctacgtg    5520
ttcgggcgct accccgcaga cctgtctggc tatgccgatc agggcaacgg ccgcaggcag    5580
tacccggtgg ttgacctcgt ggtctgccac ggcgacttcc tcaacgccga tcacaactac    5640
gtccataaga acaagagcgt aaagggcttt ggcacctacg gcgacatcat gatccgcgac    5700
cggaagatgt acgtcgcgcc gacgccattt gcgctgaccg aaggcaccac tggcctgatg    5760
actttgatcc tgccggagaa cttcggcacc gatgaccgtt accaggtggt cggtaacctc    5820
actcgcgtcg aggcggaaac gctggtggtt ggctacaact ttgacctgcg cacgaacgag    5880
ctgagcgcag agcgcgtgcc caatcccaac gcaggcaccc agcaccgatt cgtggcctac    5940
cggctcaagg atcaagcgag caagcctgtc tccatgactg gcacccaggt gcagcccgac    6000
gagaacaacc tgccggacga cgaatgaaca ccatcaccga caagatcggg ttcgcttacc    6060
cggttgcagc gaccgcgctg gagtgcgact tcccgctggt cgaaatcagc cagatcgccg    6120
agcaggaaag ttggcgaaag gagatcaaca ggccgatcta ccacatccac aagtggtggg    6180
cgaccagact tgggtcggtg tttcgtggca ttacccttgg tgctttgagt cagcctggta    6240
ctgacctctg ggcgcagttc tacaaaacgc acgacctggc cggtaaggta gtgctcgatc    6300
ccttcatggg cagtggcacg acgcttggcg aggccgtcaa gctgggtgcc aaggccatcg    6360
gctgcgacat caacccagtc agtaccttcc tcgtacgtca ggcgttcacg ccggcgtccg    6420
aggcagagct gcgtgccgct ttcgagcggc tggaacgtga cgtggcaccg gagattcggc    6480
gctactacca gacgcgcgat cctaagacgg gcgagctgat tcaggtcttg tactacttct    6540
gggtcaagac ggtgacgacg cccgagggcg aggtaatccc cttgctgtcg cgctacgtgt    6600
tttcacaaga cgcctacccg aagaagaagc gcgagcgca gatcgtgtgc cctggctgct    6660
ggagtgtgct ggaggatcgc tacgatgcga ctgacctgca ctgccagcac tgcggccacc    6720
agttcaatcc gcaggaaggc ccggccgctg gtcagtacgt caaaaccaag ggcggtcacc    6780
gttaccgcat caaggaacta ctgccaaagg acggtacgcc gccctctcat cgaatgtacg    6840
cgatgatggc cttgcgagcg gatggatcga aggtctatct gccggtgcgg aatgaggact    6900
tggccctcta cgaggaagcc caagaacgcc ttgctacaga ggcactgccg ctgccgaaaa    6960
cctctgttcg acctgccac aacaccgacc aggcgcgcgg ctacaactac acccaatggc    7020
gcgacttctt caatgcgcgc caactgctgt gccttggcct gctgctgcgg gaaatcctga    7080
ccatcgacga cctggcagtg caagagcaga tgctgtgctt gttctccagc accttggagt    7140
tcaacaacct gttttgcagc ttcaagggtg agggaacagg ggccgtgcgg catatgttct    7200
cgaaccacat cctcaagcca gagcgcaccc cgctggagaa ctccgtgtgg ggcactggca    7260
agagcagcgg tacgtttagc acgttgttcg agtctcgcct gctacgtgcg aagcgctacc    7320
tcgatgagcc gttcgagatc gcgttcgagc atgaccagga cggtaaccgc gcaggctcgc    7380
gcaagacggt ggctagccat ccgatccgcg cccgtcgcgt cgaaacctgg ccggaattgg    7440
aggccgcaga tcatggcctg ctgatcctca acggtgcaga ctcgaagctg ccggtgcccg    7500
ctggttcggt ggatgccgtg gtgactgatc cgccctactt cgacttcgtt cattactcgg    7560
agttgagcga cttctttttt gcttggctca ccccctgtgct gcgccagcgc tatccgtgga    7620
tggcccgcga ggactcgtct gaccaagggg aggtgcagca caaagaccct cgtgtgttcg    7680
```

```
cccgtcagct tgcgtcggtg ttcacggagg cgtgccgcgt gcttaaggac gatggagtgt    7740
tggcgttcag cttccaccac tcgcgtgccg agggctgggc ggccatctat gaagcgatca    7800
acaaggcggg cctggccgta gttgcggctc accctgtcca tgccgagctg cgcgcggcaa    7860
gtcccaagac tgcggccaaa gacccgatca gccttgatgc gattctggtg tgtcgcaaaa    7920
aggcgtttgc cctgcaccag tcgcctgcta tccaggatgt ccgccaggct gttgatgcgc    7980
tggcatcacg gctgcaagct gctggccttc gcatctcggc gggtgaccgc ttcgtgatcg    8040
gcgcagcgca aaccttgatt gcacgcgctg ctgatgacat gggcttcgac gagatcaagg    8100
ttgatcttga ggcaattcgg ctggccgtgg ggccaagggc tgcaacatca aaggctgcga    8160
gtgcgtggga tgacgatgtg cccttctgat tggctgcacg gccttgtcgg cgcatgcgtt    8220
ttgatgcag ccgctgcacg caagccgcgt ccctccgcgt aaagttcatt tatacgcaaa    8280
tacgtatttg cgtgatacaa taacgccata ttaatggagg tgcgtaaatg cggactattg    8340
ttgtggctag ccaaaaaggt ggcgtcggca agacaacgat tgcaggtcac ttgggtgtca    8400
tggccgagca gagcaaagag gggccagtgg cgctgatcga cacagaccca caaggctcgc    8460
tcgcgtcctg gtggaatgag cgaaccaatg aggcaccgct gtttgcacgg gtggaaatcg    8520
gcaagctgac cgagcacctt caggcattgt ccaaggtgg catcaagctg ccatcatcg    8580
acaccccgcc ctctgttacg gaaatgattc agcaggtgct ccgcaccgcc gacttggtac    8640
tgatccccac caggccgagt ccgcatgact tgcgcgcgt cggatctacc gtcgaactgg    8700
tggagaacgc aggcaagcga atgatcttcg tcatcaatgg ggcggcacct cgcgcgcgga    8760
tcgcgggtga ggctgccgtg gcgctttcgc agcatggcac ggttgccccc gtgacgctgt    8820
accagcgcac cgacttcgcc agctcgatga tcgacggccg caccgtccag gaaatcgacc    8880
ccaaggggcg gtcggccgaa gaaatcgggc agttgtggaa atacgtatct acacaactgc    8940
gtaaaatttg atataatacg tacatgcgta ttaatggaga tacgtaaatg gctaaaactg    9000
catctttgac tgccggcctg gtggccaaga aaggggaggc gtcccctgct acggttgtcg    9060
cggcacccca ggttcaacct atcgaagtga aggcatcggc gactggcggc ggccgggatt    9120
actacaaggc gttgaccgtc aagttggatc gtgaccgcta cgagagtctg aaaagcatgg    9180
gcgtgaagct ggacaagaag agccaggaaa tctttgtcga ggccctggat tgtggatga    9240
agtcggccgc tggccagcaa cacgcctaag aggcccctat gcgttcagtg cgctctgccg    9300
tcgaactcgc caaggagttg gccgaaaaag ccaaggcccg ccgcctagcg gcggaaaaga    9360
acgagctggg acttgaaggc ccggcgcagg caacgccgg caccactccc agcccggtga    9420
aggttgcggc cgaagtggtg ggcgagcagc cggcacgacg caagggagcg ccgaaagggc    9480
cgcgtggcct gatgccggtg catcatccaa accgcgattt cttcttgtgc gatctgtttg    9540
actacgccct aaaggatgac ggcgtgagca tggaggcccc catcttcacc ttggcaacca    9600
ggccggacac ctctgtttgg cattgggaaa gcaaggatgg gacacgcgcc atcaccgtca    9660
cgccaagcgt gaagggggagg gccacgcagt ttgataagga tttacttatt tacgtagtta    9720
gccagatgac cgaggctatc aatcgcggtc ggcctgatgc gaacaatcga accgtgcgct    9780
ttcgcgtcta tgactacttg gtctcaacca acaagccgac tggcggcaag gagtaccagc    9840
gactggagga tgccctagac aggctgcggg gtacatcgat caagacgaac atcaagacgg    9900
gtggccagcg tgtgaaggaa ggcttcggca tcgtcgatag ctggacgatc atcgagaagg    9960
cccccgacga tgaccgcatg attgccgtcg aggtcacgct ctccaagtgg cttttcaatg    10020
cagtgcaggc ccacgaggtt ctgaccatca acccggacta tttccggctg cgtaagccaa    10080
```

```
ttgagcgccg tttgtacgag ctggccagga agcactgtgg cgaccaggcc ttttttgtga    10140
ttgggctgga actgttgcag gacaagtgcg gcagcaagtc ggcactgttc gagttccgcc    10200
gtgccttgcg cgagatcatc aaggccgaca ccttgccaga ctaccgcatg acgcttgatg    10260
acgagaaaga ccaggtgatt ttctacaccc gcgacacgaa gaagctagcg gcgtctaccg    10320
ctctggcccg gcgcttccag tgacgcccaa agtattgacg gtcaatactt cgttatttca    10380
cccatgcggt gttaccgctg cgtgttggac gttcccttga cctagcggcc gaggcagggc    10440
tttcgcgctt tgcattgagc caccaagtgc gtctcgctcc ttcgagcatc aagccctaac    10500
gcgtttcatg tcactttcgc gcacgaaagt cgaggcaaga ggcttgatcg tgtctatcgt    10560
tacatcaccc atgcctgtgg atggacacgt tacatcaccc atgttttctg tggatgggca    10620
cgttacatca cccatacctc acttcgttac atcgcccatg cagcgatttg tggaagcctt    10680
gagcagcaag gctttacgag cgttatccac agccgtaaca cgcgcgcgcg attttttaac    10740
tttataaatc tttaacgcgg ttgcggacaa agcccgcgcc gcctcttggg ggctacgccc    10800
ccgccggctc ctacgggccg caagcggccc tccgcccgcg cttcgcgctc cctcccggca    10860
tccccgaggg gtttcgcttc gctgcacccc tcgcgcttcg cgctcacccg catatcgagg    10920
cccccaaagg gggccggatg gtgccccc                                     10948
```

EXTRACT AND DERMATOLOGICAL COMPOSITION COMPRISING SAME, FOR TREATING SENSITIVE SKIN

REFERENCE TO SEQUENCE LISTING SUBMITTED VIA EFS-WEB

This application includes an electronically submitted sequence listing in .txt format. The .txt file contains a sequence listing entitled "2021-06-10_3493-0738PUS1_ST25.txt" created on Jun. 10, 2021 and is 16,942 bytes in size. The sequence listing contained in this .txt file is part of the specification and is hereby incorporated by reference herein in its entirety.

FIELD OF THE INVENTION

The present invention concerns a novel bacterial extract which may be useful in the protection and/or treatment of sensitive skin and/or reactive intolerant skin, notably through targeted action on cutaneous neurogenic inflammation. The invention also concerns cosmetic or dermatological compositions containing such a bacterial extract as active agent.

STATE OF THE PRIOR ART

The epidermis is a pluristratified epithelium that acts as a protective barrier against its environment and harm. Among its multiple physiological functions, the epidermis has the function of constituting a biological, physical and chemical barrier against invasion of the body by microorganisms. This physical barrier property of the epidermis is notably linked to its structure. For example, the epidermis is conventionally divided into a basal layer of keratinocytes constituting the germinative layer of the epidermis, a so-called spinous layer consisting of several layers of polyhedral cells and finally, a set of upper layers called the horny layer (or stratum corneum), consisting of keratinocytes in the terminal stage of their differentiation called corneocytes. The chemical barrier properties of the epidermis depend, in particular, on the release at the surface of the epidermis of many antimicrobial peptides. A dysfunction in the epidermal cellular structural organization, or a defect in the chemical barrier function of the epidermis, can result in a cutaneous inflammatory state.

Inflammation is a normal immune defense reaction of the body to an insult of the following types: infectious, thermal, mechanical, chemical, lesional or allergic. It is characterized by four points: redness, heat, swelling and pain. Acute skin inflammation is an immediate response to a harmful agent, of short duration (a few days or weeks), often with a sudden onset and characterized by intense swelling. Acute inflammations heal spontaneously or with treatment. Chronicity occurs when the inflammation does not heal spontaneously, persists or worsens for several months or even years. The inflammatory reaction is a dynamic process involving several successive steps: vascular (vasodilation), leukocyte extravasation and immune cell chemotaxis and finally cleansing. Leukocyte extravasation refers to the active crossing of vascular walls and the accumulation of circulating immune cells, lymphocytes, neutrophils and monocytes in the lesion site. Neutrophils have the function of attracting other inflammatory cells by chemotaxis and of cleaning the injured site by secreting antimicrobial substances and proteases. Monocytes migrate by chemotaxis and differentiate into macrophages which clean the damaged area. They secrete growth factors, inflammatory cytokines, such as IL-1, notably IL-1β, TNFα, proteases, prostaglandins and IFNs allowing the maintenance and/or amplification of inflammation. Cleansing follows the vascular phase and is contemporary with leukocyte extravasation. This is a process in which necrotic tissue and pathogens are removed.

Cutaneous neurogenic inflammation is defined as the induction and/or amplification of a primary inflammatory process by nerve endings, thus it is an inflammation of the skin induced by the activation of intraepidermal nerve fibers that secrete neuropeptides such as substance P. Cutaneous neurogenic inflammation is particularly involved in sensitive skin, reactive intolerant skin and in pruritic inflammatory dermatoses. Pruritus is defined as an unpleasant sensation that causes the need to scratch. Recently, the notion of itch receptors (pruriceptors), specific receptors for perceiving itch, has emerged, but their distinction from the family of nociceptors is still being debated. These pruriceptors use intraepidermal Aο-fibers and especially C-fibers. They secrete neuropeptides: substance P, calcitonin gene-related peptide (CGRP) and vasoactive intestinal peptide (VIP). Recently, the role of proteases (trypsin, cathepsin G, thrombin, etc.) in the induction of pruritus has been clearly established. Indeed, protease-activated receptor 2 (PAR-2) has been defined as the second major pathway for pruritus activation (Misery et al., Nat. Rev. Neurol 10, 408-416, 2014).

Intradermal nerve fibers interact directly or indirectly with skin cells and cells of the endocrine, lymphatic and immune systems. These communications led to the definition of a neuro-immuno-cutaneous-endocrine system. To function, this system requires a common language made up of molecules of different natures, neurotransmitters, cytokines and growth factors. These molecules are synthesized and released by skin cells, resident and recruited immune cells, and intraepidermal nerve endings. Epidermal and dermal cells can also produce neurotransmitters, enzymes, neurotrophins, cytokines, chemokines and growth factors. These mediators regulate skin innervation and the inflammatory response. In the event of inflammation, immune cells in transit or constitutively present in the skin can be activated by the action of these mediators secreted by sensory nerve endings and skin cells. This process leads to a second wave of release of cytokines and neurotransmitters, which generate an amplification loop of the inflammation.

A novel concept has recently emerged, suggesting that keratinocytes are also major actors in cutaneous neurogenic inflammation.

Cutaneous neurogenic inflammation generated by neuropeptides is involved in the reactivity of sensitive skin and also intolerant skin. The notion of sensitive skin reflects the sensitivity level of each person's skin. While it is possible to have sensitive skin at any age, this is extremely common in babies and the elderly. Babies' skin is about one-fifth the thickness of adult skin and is therefore extremely sensitive to chemical, physical and microbial damage, as well as to UV rays. The barrier function of adult skin gradually weakens with age, as metabolic processes slow down. As the skin ages, it gradually becomes deficient in lipids, which makes it more easily irritated by alkaline substances such as soap.

When the skin has a very low sensitivity threshold, i.e. it overreacts to the slightest external insult, this is referred to as intolerant skin, or reactive intolerant skin. Intolerant skin is more vulnerable to external insult and is characterized by daily discomfort and high irritability. Some signs, more or less marked, make it possible to recognize it. Intolerant skin of the face, for example, is red and tingles. It pulls, heats or itches. It can also cause burning sensations. Intolerant skin is generally allergic and is therefore particularly sensitive to the components of cosmetic care products.

Sensitive skin is in fact skin prone to pins and needles, overheating, tingling and itching, sometimes accompanied by redness. These feelings of discomfort appear in an exacerbated way in response to stimuli that would not trigger irritation in normal skin. This hypersensitivity of the skin results from a decrease in its tolerance threshold. The more sensitive the skin, the lower its tolerance threshold, and when the tolerance threshold is at its lowest, this is referred to as intolerant skin. This hypersensitivity can be explained by various factors:

An inflammatory reaction that develops when in contact with chemical irritants such as certain soaps, household detergents or pollution; the threshold triggering these substances thus evoking sensitive or intolerant skin.

An alteration of the epidermal barrier function. This phenomenon then promotes dehydration of the skin and especially the penetration of potential irritants;

Psychological factors, such as stress;

Hormonal factors;

Physical factors such as sunlight, temperature changes (hot/cold), wind, air conditioning, heating, hard water.

The skin is covered with a protective film, called a surface hydrolipidic film. This film is the outermost barrier, a barrier which is also the most fragile, the most disturbed and the most representative of skin health; it consists mainly of fatty substances excreted by the sebaceous glands and lipids resulting from the degradation of cells during the keratinization phase of horny cells, as well as hydrophilic compounds, such as sweat water, glycerol, urea, natural skin moisturizing factors, salts, metabolites of the skin flora, etc. This surface film is highly exposed and sensitive to environmental stresses, hygiene habits, and skin conditions. It is important to preserve, and even improve, this barrier function, especially for the most sensitive skin. And, while it is known that populations with intolerant skin whose skin barrier is weakened require care with physio-mimetic hydrolipidic agents, particularly emollients and physiological moisturizers, it is also important to avoid bringing the skin into contact with any substance likely to degrade the surface hydrolipidic film, such as a surfactant or a preservative.

Sensitive or intolerant skin is a non-allergic mechanism and involves an inflammatory reaction without recognition of a specific allergen.

The pathophysiological mechanisms of skin hyperreactivity are not clearly elucidated, but there is a tendency to identify two types of factors that may be contributing. On the one hand, there is the alteration of the skin barrier through water loss and the alteration of intercorneocyte lipids. The skin becomes more sensitive to external irritants and stimuli and irritation, even minimal, leads to the release of inflammatory cytokines and compounds from the arachidonic cascade. On the other hand, a neurological disorder may be responsible for the sensitivity and reactivity of the skin. Nerve fibers reaching the cells of the epidermis produce, under the influence of external stimuli, neurotransmitters (such as substance P) that cause neurogenic inflammation, i.e. cutaneous neurogenic inflammation.

There is thus a need for a composition capable of treating, preventing and protecting sensitive skin, intolerant skin whose inflammatory component is neurogenic inflammation.

The object of the present invention is to meet these needs, in other words to propose a composition that protects and/or improves the condition of sensitive skin, or of intolerant skin, by reducing or inhibiting cutaneous neurogenic inflammation.

For the first time, the applicant has demonstrated the beneficial properties in tissue regeneration and healing of skin lesions of a bacterial extract derived from a bacterial strain (or bacterium) LMB64 isolated from groundwater. This bacterium was described by the applicant in patent application WO2012/085182. More particularly, the extracts known as S0, E0 and ES0 were described and exemplified, respectively consisting of the culture supernatant separated from the biomass, the lysed cell biomass, and the supernatant after incubation of the culture at basic pH for several hours. Fractions E0 and ES0 were tested and it was shown that these extracts E0 and ES0 had the ability to induce cytokines and mature Langerhans cells (for E0) as well as activate TLR2/TLR4/TLR5 receptors, antagonize PARs and induce antimicrobial peptides (for ES0). These results made it possible to consider the use of such extracts in the treatment of inflammatory diseases such as pruritus, psoriasis, eczema or atopic dermatitis.

SUMMARY OF THE INVENTION

The inventors have surprisingly revealed the effectiveness of a particular novel bacterial extract in preventing and/or treating cutaneous neurogenic inflammation.

Indeed, the inventors have demonstrated that this bacterial extract has an inhibitory effect on the release by keratinocytes of IL-1$\beta$ and TNF-$\alpha$ induced by substance P.

DETAILED DESCRIPTION

According to a first embodiment, the object of the present invention is a bacterial extract according to the invention and the use of same in the prevention and/or treatment of cutaneous neurogenic inflammation.

In particular, the prevention and/or treatment of cutaneous neurogenic inflammation comprises, or consists of, the protection and/or treatment of sensitive skin or intolerant skin.

In particular, the prevention and/or treatment of cutaneous neurogenic inflammation comprises, or consists of, the protection and/or treatment of sensitive skin.

In particular, the prevention and/or treatment of cutaneous neurogenic inflammation comprises, or consists of, the protection and/or treatment of intolerant skin.

The bacterium LMB64 has been characterized and defined as belonging to the class Beta-proteobacteria, subfamily Neisseriaceae, and probably of a new genus not yet defined. Analysis of the sequence of the gene coding for 16S ribosomal RNA (rRNA) has made it possible to locate this bacterium close to the genera *Chromobacterium, Paludimonas, Lutelia* and *Glubenkania*, with which it shares 95% sequence similarity. This non-pathogenic, Gram-negative bacterium has been isolated from groundwater. More specifically, bacteria LMB64 is rod-shaped with a length of about 2.3 μm±0.3 μm and a width of about 1.0 μm±0.1 μm. A particular feature of this bacterium is the presence of a polar flagellum.

The gene coding for 16S rRNA was almost completely sequenced (1487 bp, corresponding to sequence SEQ ID NO: 1). Bacterium LMB64 has a circular plasmid of 10948 bp. This plasmid has been fully sequenced, and the sequence is shown in SEQ ID NO: 2.

According to another embodiment, a bacterium from which a bacterial extract according to the invention is derived comprises at least one plasmid comprising sequence SEQ ID NO: 2, or any sequence having at least 80% identity with sequence SEQ ID NO: 2, advantageously at least 85%, at least 90%, at least 95%, or at least 97% and more preferentially at least 98% identity with sequence SEQ ID NO: 2.

Also, a bacterium from which the bacterial extract according to the invention is derived is a non-pathogenic Gram-negative bacterium belonging to the class Betaproteobacteria, subfamily Neisseriaceae, said bacterium comprising a 16S rRNA comprising sequence SEQ ID NO: 1, or any sequence having at least 80%, or at least 90%, at least 95%, at least 97% identity with sequence SEQ ID NO: 1 and said bacterium comprising at least one plasmid comprising sequence SEQ ID NO: 2, or any sequence having at least 80% identity with sequence SEQ ID NO: 2, advantageously at least 85%, at least 90%, at least 95%, or at least 97% and more preferentially at least 98% identity with sequence SEQ ID NO: 2.

By way of example, such a bacterium is represented by strain LMB64 which was deposited on behalf of the applicant at the Collection Nationale de Cultures de Microorganismes (CNCM), Institut Pasteur, Paris, on 8 Apr. 2010 under number 1-4290.

Having this genotypic information, combined with the growth characteristics on sulfur-free media, the nonfilamentous nature of this bacterium, a skilled person would have no difficulty in finding/identifying another bacterium allowing a bacterial extract according to the invention to be obtained. Such identification of another bacterium, which may be slightly different genotypically but which meets the phenotypic criteria of the invention as regards the bacterial extract, can be carried out after a selection process which is in no way insurmountable, on the basis of the information contained in the present application and that contained in application WO2012/085182 combined with the general knowledge of the skilled person.

In the context of the invention, "percentage identity" between two nucleic acid sequences refers to a percentage of identical nucleotides between the two sequences to be compared, obtained after the best alignment (optimal alignment, this percentage being purely statistical and the differences between the two sequences being distributed at random and over their entire length. Sequence comparisons between two nucleic acid sequences are traditionally carried out by comparing these sequences after they have been optimally aligned, which can be done by segment or by "comparison window". Optimal alignment of the sequences for comparison can be achieved, in addition to manually, by means of the local homology algorithm of Smith and Waterman (1981) [Ad. App. Math. 2:482], by means of the local homology algorithm of Needleman and Wunsch (1970) [J. Mol. Biol. 48:443], using the Pearson and Lipman (1988) similarity search method [Proc. Natl. Acad. Sci. USA 85:2444], using computer software using these algorithms (GAP, BESTFIT, FASTA and TFASTA in the Wisconsin Genetics Software Package, Genetics Computer Group, 575 Science Dr., Madison, WI, or by the BLAST N or BLAST P comparison software).

The percentage identity between two nucleic sequences is determined by comparing these two optimally aligned sequences in which the nucleic acid sequence to be compared may include additions or deletions with respect to the reference sequence for optimal alignment between these two sequences. The percentage identity is calculated by determining the number of identical positions for which the nucleotide is identical between the two sequences, dividing this number of identical positions by the total number of positions in the comparison window and multiplying the result by 100 to obtain the percentage identity between these two sequences.

For example, the BLAST program can be used, specifically "BLAST 2 sequences" (Tatusova et al., "Blast 2 sequences—a new tool for comparing protein and nucleotide sequences", FEMS Microbiol Lett. 174:247-250) available on the website http://www.ncbi.nlm.nih.gov/gorf/b12.html, the default parameters are used (in particular for the parameters "open gap penalty": 5, and "extension gap penalty": 2; the matrix chosen is for example the matrix "BLOSUM 62" suggested by the program). The percentage identity between the two sequences to be compared is calculated directly by the program. It is also possible to use other programs such as "ALIGN" or "Megalign" (DNASTAR).

A bacterium according to the invention, in particular bacterium LMB64, comprises at least one plasmid comprising sequence SEQ ID NO: 2, or any sequence having at least 80%, preferably 85%, 90%, 95% and 98% identity with said sequence SEQ ID NO: 2. Other characteristics of said bacterium, in particular bacterium LMB64, will be detailed below in the examples.

In general, the term "bacterial extract according to the invention" is used to describe the set comprising the soluble compounds present in the cytosol of the bacterium, obtained after the isolation of the bacterial cells from the fermentation medium, their lysis, in particular by freezing-thawing, a resuspension in an aqueous solvent and recovery of the liquid fraction comprising cytosolic components, soluble intracellular cell compounds, soluble membrane compounds/molecules, soluble transmembrane compounds/molecules, soluble periplasmic compounds/molecules and soluble flagellar compounds/molecules, in particular proteins.

The expression "soluble membrane compounds/molecules, soluble transmembrane compounds/molecules, soluble periplasmic compounds/molecules and soluble flagellar compounds/molecules" refers to proteins and other soluble compounds contained in the cytoplasmic or periplasmic space, in the membrane or transmembrane space or in the flagella, and which are released by the lysis of a bacterium according to the invention. These proteins and compounds are obtained by the process according to the invention, in other words the recovery of the liquid phase following a liquid/solid separation carried out on the cell mass of lysed bacteria, for example by freeze-thawing, after isolation of this cell mass from the fermentation medium. These soluble cytosolic, membrane, periplasmic and/or flagellar intracellular proteins or compounds include, for example, ribosomes, enzymes associated with cellular metabolism, lipopolysaccharides, sugars, lipoproteins, membrane and periplasmic, released by lysis and soluble in water or an aqueous solvent.

Bacteria multiply by binary fission, meaning that each bacterium grows and then divides into two daughter cells separated by a dividing septum formed by the cell wall. During division, DNA duplicates itself and the other components. Various enzymatic systems of synthesis and degradation participate in cell division.

Bacterial growth is the ordered increase of all components of the bacteria. It leads to an increase in the number of bacteria. During growth, the culture medium is depleted of nutrients and enriched in biomolecules secreted and excreted in the culture medium by the bacteria and solubilized in this medium as well as in metabolic by-products.

The expression "culture medium" refers to any medium containing at least the nutrients necessary for bacterial growth and multiplication. Bacteria can be grown in liquid, solid or semi-liquid media. Preferably, the culture medium is a liquid medium allowing the growth and recovery of biomass and allowing the production of a bacterial extract according to the invention.

An adequate culture medium contains nutrients that promote bacterial growth and multiplication. In general, a suitable growing medium may include water a carbon source, a nitrogen source and salts.

Mention may be made of the "fermentation medium" or bacterial culture which corresponds to the culture medium containing bacteria at the end of their growth and development.

In practice, the bacterial extract according to the invention, in particular an extract of bacterium LMB64, can be obtained from a culture of a bacterium according to the invention in a culture medium allowing the growth, development and multiplication of said bacterium and the recovery of the cells after their separation from the liquid phase, for example centrifugation, in the form of a pellet or biomass. This biomass is subjected to a treatment to permeabilize and degrade cell membranes and walls—for example by freeze-thaw. The extract according to the invention can be obtained by taking the treated biomass, in particular thawed, with a basic buffer and then carrying out a solid/liquid separation of the mixture, for example by centrifugation. An aqueous phase representing the extract according to the invention is thus obtained.

The biomass can be recovered from the fermentation medium by any means of liquid/solid separation. More specifically, it is therefore possible, using techniques known to persons skilled in the art, to isolate the cellular biomass containing mainly whole cells, cell debris comprising surface proteins and/or proteins located in the periplasmic space of the bacterium from the liquid fraction containing residual solutes from the culture medium and biomolecules excreted by the bacteria and solubilized in the fermentation medium.

By way of illustration, liquid/solid separation can be carried out by a technique chosen from: centrifugation, sedimentation, filtration, ultrafiltration, settling.

Preferably, liquid/solid separation is carried out by centrifugation fermentation medium containing the bacterial culture in order to separate, on the one hand, the solid phase, i.e. the biomass pellet, containing cells and cell debris and, on the other hand, the liquid phase, i.e. the supernatant comprising the soluble molecules excreted during fermentation and residual compounds of the culture medium not consumed by the bacteria.

The solid phase, i.e. the biomass obtained, in particular the centrifugation pellet, is subjected to a step leading to the rupture of the cell membranes, for example freezing, followed by thawing.

Freezing can be carried out at any negative temperature allowing water to solidify, intracellular and intermembrane crystals to form and, therefore, the membranes to at least partially rupture.

In particular, freezing can be carried out at a temperature of −10° C., or −20° C., or −30° C., −40° C., −50° C., −60° C. or about −80° C. Preferentially, freezing is done at about −20° C.

Freezing time and speed are not critical in themselves. The freezing time may depend on the temperature and for example a period of one to several hours is appropriate. The frozen solid phase can also be stored for several days, weeks or months, even if it is not necessary.

The rate of freezing, or of thawing, is also not critical and conditions will be sought to allow the alteration of bacterial walls and membranes.

The term "thawing" means to a return to a positive temperature that allows the ice crystals to melt.

This step of permeabilization and rupture of walls and membranes can also be carried out by chemical, ultrasonic or mechanical means such as detergents, chaotropic agents, glass beads, for example.

This step allows the release of soluble cytoplasmic intracellular compounds that are therefore present in this solid phase of lysed or damaged cells.

To this solid phase is then added a liquid phase in the form of an aqueous solvent to resuspend the lysed or damaged cells and extract the cytoplasmic soluble compounds soluble in said solvent.

The aqueous solvent is preferentially a buffer, in particular a basic buffer. Preferably this basic buffer is a Tris buffer or an arginine buffer or a Tris-arginine buffer. Preferably it is an arginine buffer. The arginine concentration may be comprised between 0.1 and 1 M, particularly between 0.3 and 0.5 M. The Tris concentration may be comprised between 1 and 100 mM, particularly 20 mM. The pH of the basic buffer may be between 8 and 12, and preferably between 9 and 11.

This resuspension step allows the extraction of cytoplasmic soluble compounds contained in the biomass of lysed or damaged cells.

Finally, liquid/solid separation is performed to recover a liquid aqueous phase, in particular a buffered liquid aqueous phase, containing soluble cytoplasmic intracellular compounds.

This liquid phase obtained thus represents the extract according to the invention.

The solid phase/aqueous liquid phase ratio for the resuspension step may be comprised between 1 and 10% w/v.

The use of a basic buffer makes it possible to make the external membranes even more permeable and to promote the diffusion of molecules from the periplasmic space to the liquid medium. The use of a basic buffer also makes it possible to stabilize the compounds, in particular soluble proteins, and to prevent them from aggregating over a long storage period and from degrading by the action of proteases.

One or more filtration steps may be performed to clarify the extract and result in a purified extract according to the invention.

Filtration may be carried out by any appropriate means allowing clarification of the liquid phase, or the buffered liquid phase. Such clarification by filtration allows the removal of suspended particles that would not have been removed in the second liquid/solid separation step and aims at producing a purified, clear bacterial extract according to the invention.

Filtration can be carried out by any means of filtration, ultrafiltration or diafiltration.

Advantageously, filtration is carried out by filtration on a filter or filter cartridge having a cut-off of 0.4 µm, preferably 0.2 µm. In this case, the bacterial extract is characterized in that the compounds present in the bacterial extract have a size less than or equal to 0.2 µm.

Preferably, electrostatically uncharged filters or prefilters may be used to avoid any absorption of the biomolecules responsible for all or part of the extract's activity.

The different steps will be described in more detail in the examples. It must be understood that any modification of the process, media or sequence of steps that seems obvious to a skilled person with regard to the present description must be considered as falling within the scope of the present invention.

According to one embodiment, the process according to the invention consists of a process for preparing a bacterial extract according to the invention, said process comprising the steps of:
- a) culture of a bacterium according to the invention, in particular LMB64, in a suitable medium to obtain a bacterial culture;
- b) liquid/solid separation of said culture and removal of the liquid phase;
- c) cell lysis of the solid phase,
- d) resuspension of the lysed solid phase in an aqueous liquid phase, preferentially buffered,
- e) liquid/solid separation and recovery of the liquid phase,
- f) optional filtration of the liquid phase. In a preferred embodiment, step c) of cell lysis of the solid phase is performed by freezing followed by thawing.

According to a particular embodiment, the bacterium is a non-pathogenic Gram-negative bacterium belonging to the class Betaproteobacteria, subfamily Neisseriaceae, comprising a 16S rRNA comprising sequence SEQ ID NO: 1, or any sequence having at least 80% identity with sequence SEQ ID NO: 1, more particularly it is bacterium LMB64.

Preferentially, the bacterium comprises at least one plasmid comprising sequence SEQ ID NO: 2, or any sequence having at least 80% identity with sequence SEQ ID NO: 2.

According to one embodiment, the present invention concerns a bacterial extract obtained, or obtainable, by a process according to the invention as described above.

In one embodiment, the invention concerns a bacterial extract according to the invention, in particular an extract obtained or obtainable by a process according to the invention, for use in the prevention, treatment, prevention and treatment of cutaneous neurogenic inflammation.

Advantageously, the cutaneous neurogenic inflammation includes sensitive skin and/or intolerant skin.

According to another embodiment, the invention concerns a cosmetic or dermatological composition comprising at least one bacterial extract according to the invention, with at least one cosmetically or dermatologically acceptable excipient, for use in the prevention, treatment, prevention and treatment of cutaneous neurogenic inflammation.

According to another embodiment, the invention concerns a cosmetic or dermatological composition comprising at least one bacterial extract according to the invention, with at least one cosmetically or dermatologically acceptable excipient, for use in the protection and/or treatment of sensitive or intolerant skin. In particular, this is sensitive or intolerant skin the origin of which is cutaneous neurogenic inflammation.

The invention also concerns the use of a cosmetic or dermatological composition comprising at least one bacterial extract according to the invention, with at least one cosmetically or dermatologically acceptable excipient, for the manufacture of a medicinal product intended for the prevention, treatment, prevention and treatment of cutaneous neurogenic inflammation.

The invention also concerns a method for preventing and/or treating cutaneous neurogenic inflammation comprising administering to an individual in need thereof an effective amount of a cosmetic or dermatological composition comprising at least one bacterial extract according to the invention, with at least one cosmetically or dermatologically acceptable excipient.

Advantageously, the cutaneous neurogenic inflammation includes sensitive skin and/or intolerant skin.

In the present invention, "cosmetically or dermatologically acceptable" means that which is useful in the preparation of a cosmetic or dermatological composition which is generally safe, nontoxic and neither biologically nor otherwise undesirable and which is acceptable for cosmetic or dermatological use, notably by topical application.

According to a particular embodiment, the composition according to the invention is in a form suitable for topical application.

The cosmetic or dermatological compositions according to the invention may be in the forms that are generally known for topical administration, i.e. lotions, foams, gels, dispersions, emulsions, sprays, serums, masks or creams, jellies, in particular micellar jellies, with excipients allowing in particular skin penetration in order to improve the properties and accessibility of the active principle. Advantageously, it will be a cream, a rich cream, a lotion, an eye care product, a UV care product.

These compositions generally contain, in addition to the compounds of the bacterial extract according to the invention, a physiologically acceptable medium, generally based on water or solvent, for example alcohols, ethers or glycols. They may also contain surfactants, complexing agents, preservatives, stabilizers, emulsifiers, thickeners, gelling agents, humectants, emollients, trace elements, essential oils, fragrances, dyes, matting agents, chemical or mineral filters, moisturizers, thermal waters, etc.

Advantageously, the compositions according to the present invention will comprise 0.05 to 10 wt %, preferably 0.1 to 5 wt %, more preferably 0.5 to 3 wt % of the bacterial extract according to the invention based on the total weight of the composition.

The composition according to the invention provides protection that remains comfortable all day long. It can in particular be applied to sensitive skin, reactive skin, and notably baby's skin.

Preferably, the composition according to the present invention is used to prevent, protect and/or treat sensitive skin.

In general, sensitive skin is defined by a particular reactivity of the skin. This skin reactivity is classically expressed by the manifestation of signs of discomfort in response to the subject's contact with a triggering element that can have various origins. This may involve the application of a cosmetic product to the surface of sensitive skin, food intake, exposure to sudden temperature changes, air pollution and/or ultraviolet or infrared rays. There are also factors associated with age and skin type. Thus, sensitive skin is more common among dry or oily skin than among normal skin. In the sense of the present invention, sensitive skin covers irritable and intolerant skin.

Such compositions can be manufactured according to processes well-known to the skilled person.

The invention will be better understood by reading the examples below which illustrate it without limiting its scope.

EXAMPLE 1

Culture of Bacteria LMB64

By way of example, preferred culture media contain ammonium chloride, magnesium sulfate and yeast extract. It should also be noted that, as shown in application WO2012/085182 and others, other similar media may be used and should therefore be considered as an integral part of the present description. Any adaptation by persons skilled in the art must also be considered as part of the invention.

An example of a culture process is described below. It should be recalled here that this example is only illustrative and should in no way be considered limiting.

Strain LMB64 is grown in three steps, namely a first inoculum, a preculture (or prefermentation) in batch mode and finally a culture but in fed-batch mode (addition of glucose).

Inoculum: A tube of WCB LMB64 is used to inoculate an Erlenmeyer flask containing 1000 mL of sterile medium. The Erlenmeyer flask is then placed in the shaker incubator with shaking. When the cell density of the broth is sufficient, the culture is stopped. The cells are then cooled until they are transferred to the prefermenter.

Preculture: the prefermenter is then filled with about 16 L of medium and fully sterilized.

Two satellite vials are connected to the prefermenter after sterilization of the tank and then adding blocks:

A vial containing a sterile 50% glucose solution. This solution (glucose batch preculture) is immediately transferred to the culture medium to reach the initial glucose concentration of 20 g/L.

The Erlenmeyer flask containing the inoculum described above in the Inoculum step is inoculated in the prefermenter.

Preculture is started and then regulated automatically. By way of example, the following parameters may be mentioned: temperature, stirring speed, pressure, air flow rate or $pO_2$.

Cell growth is monitored by a measurement of the optical density at 620 nm. The preculture is stopped by cooling when it reaches a sufficient density.

Culture: the fermenter is then filled with 127 L of medium adjusted to pH 7.0 and fully sterilized. Three satellite vials are used:

A vial containing a sterile glucose solution. This solution is immediately transferred to the culture medium to reach the initial glucose concentration of 20 g/L.

A bottle of defoamer. This defoamer will be added automatically during culture to control the level of foam in the tank.

A bottle of fed-batch glucose. This solution will be added during culture to support cell growth.

The culture is started and then regulated automatically. By way of example, the following parameters may also be mentioned: temperature, pH, stirring, pressure, air flow rate, $pO_2$.

After exhaustion of the glucose initially present in the medium (rise in Po2), the addition of the fed-batch glucose solution is triggered and allows high-density cell growth. Fermentation is stopped after total glucose consumption. At this stage, the fermentation must is automatically cooled. Throughout the culture, cell growth is monitored by a measurement of the optical density at 620 nm. The amount of dry biomass (g/L) obtained at the end of culture is determined using a weight method.

EXAMPLE 2

Extraction of the Fraction According to the Invention

The example below is given as an illustration of a preferred embodiment, but should not be considered limiting.

The bacterial extract according to the invention is generally obtained after centrifugation of the result of the culture step in order to eliminate the supernatant and to keep the biomass, i.e. the cells, surface proteins, proteins located in the periplasmic space and intracellular proteins of the bacteria (presence due to the freezing step). For the centrifugation step, the transfer line from the fermenter to the centrifuge is sterilized. The fermentation must is then separated by continuous centrifugation on a centrifuge. Centrifugation is carried out at 150 L/h (±30 L/h) with a bowl speed of 10900±1000 rpm. The cells are collected in a single-use bag. The supernatant is removed during ultra-pasteurization. This centrifugation step is followed by a step of freezing the pellet at −20° C. for at least 1 hour.

One hundred and ten liters of Tris Arginine extraction buffer is sterilized in the fermenter. Cells previously thawed at room temperature are transferred to the fermenter via the peristaltic pump. The contact time required is comprised between 1 and 7 hours. The target concentration of Tris and arginine after addition to the single-use bag is around 0.3M L-arginine and 20 mM Tris.

The fermentation must is then separated by continuous centrifugation on a centrifuge. Centrifugation is carried out at 100 L/h (±30 L/h) with a bowl speed of 10900±1000 rpm. Partial settling is automatically initiated according to the turbidity of the effluent with a set point at 20% turbidity. A series of total settling operations is manually triggered at half the volume to be separated. The supernatant is collected in a single-use bag. The cells are removed during ultra-pasteurization.

Two filtration steps are carried out in line, in order to clarify the supernatant and to result in a germ-free bacterial extract according to the invention. The filtration is controlled by the filtration/distribution system. The single-use depth filter cartridge is placed in its filter housing. The filtration manifolds are equipped with their pressure gauges to ensure the safety of the filtration stage. The prefiltration module is rinsed with approximately 92 L±5 L of purified water and the bag of product to be filtered is connected and shaken. Finally, the 0.2 µm30" PES filtration cartridge is connected to the rest of the filtration system. Filtration is carried out at an initial flow rate of 240 L/h±10 L using a peristaltic pump. When the pressure upstream of the filters reaches 1.2 bar, the filtration flow rate is reduced. The totality of the filtered product is collected sterile in a container equipped with a 400 L single-use bag. The bag of filtered product is weighed on the balance pan and stored at +5° C. until distribution. After use, the sterilizing filter is disconnected and checked by an integrity test.

EXAMPLE 3

Effect of the Bacterial Extract According to the Invention on Cutaneous Neurogenic Inflammation The purpose of this study is to evaluate the modulatory properties of the bacterial extract according to the invention in skin inflammation. To that end, an in vitro experimental approach based on the measurement of production and release of tumor necrosis factor-alpha (TNF-α) and interleukin-1 beta (IL-1β) by human epidermal keratinocytes, activated by substance P, is proposed as an in vitro model of cutaneous neurogenic inflammation.

Protocol

The study is carried out on normal human epidermal keratinocytes; these cells are obtained from newborn foreskin. These cells are cultured in a serum-free medium using conventional laboratory procedures. The determination of markers of cutaneous neurogenic inflammation is carried out on these keratinocytes cultured in a medium in the absence (control condition) or in the presence of the compounds to be tested (bacterial extract according to the invention and reference product), and optionally exposed to substance P. The keratinocytes are treated 3 hours before the stress induced by substance P and during the following 24 hours. Levels of proinflammatory cytokines (TNF-α and IL-1β) are quantified 24 h after the induction of inflammatory stress by the addition of substance P (0.5 μM). At the same time, compound CP96345, a selective NK-1R inhibitor, is tested at 1 μM as reference product. Each experimental condition is conducted on two different keratinocyte donors.

TNF-α and IL-1β productions are measured in the incubation media and quantified by the enzyme-linked immunosorbent assay (ELISA). Statistical analysis (*p<0.05; p<0.01 or *p<0.001) is determined on the percentage inhibition using a non-parametric test because the data do not pass the normality test, followed by Dunn's multiple comparison test as a post-hoc test.

The results on IL-1β release (pg/mg total protein) are summarized in Table 1 below:

| Groups | conc | IL-1β (pg/ml) | | | |
|---|---|---|---|---|---|
| | | mean | SE | % Inh | Stats |
| Cont SP(−) | | 122.2 | 11.8 | — | p < 0.001 |
| Cont SP(+) | | 241.2 | 18.3 | | |
| NK-1R inh | 1 μM | 132.5 | 12.1 | 91 | p < 0.05 |
| Compound | 1.64 μg/ml | 143.2 | 9.2 | 80 | NS |
| according | 5.45 μg/ml | 127.7 | 8.4 | 93 | p < 0.05 |
| to the invention | 16.36 μg/ml | 125.7 | 10.2 | 96 | p < 0.01 |

Conc: concentrations, Inh: inhibition, Stats: statistics versus Cont (+); SE: Standard error of the mean; Cont: control (without test product); SP(−): without substance P; SP(+): in the presence of substance P.

Exposure of keratinocytes to substance P induces a substantial and statistically significant release of IL-1β. Treatment with CP96345 at 1 μM strongly reduces (91%, p<0.05) IL-1β production. This result is very convincing: the use of this NK-1R inhibitor validates this test. The treatment of keratinocytes with the compound according to the invention allows concentration-dependent inhibition of IL-1β release induced by substance P. While the first concentration tested (1.64 μg/ml protein) does not reach significance, it still reduces this IL-1β release by 80%. At concentrations of 5.45 μg/ml and 16.36 μg/ml (μl/ml protein), this inhibition is statistically significant (93% and 96% inhibition, p<0.05 and p<0.01, respectively).

The results on TNF-α release (pg/mg total protein) are summarized in Table 2 below:

| Groups | conc | TNF-α (pg/ml) | | | |
|---|---|---|---|---|---|
| | | mean | SE | % Inh | Stats |
| Cont SP(−) | | 4.1 | 0.7 | — | p < 0.01 |
| Cont SP(+) | | 9.9 | 0.8 | | |
| NK-1R inh | 1 μM | 4.6 | 0.9 | 90 | p < 0.001 |
| extract | 1.64 μg/ml | 6.1 | 0.5 | 63 | NS |
| according | 5.45 μg/ml | 5.9 | 0.6 | 68 | NS |
| to the invention | 16.36 μg/ml | 5.4 | 0.6 | 77 | p < 0.01 |

Conc: concentrations, Inh: inhibition, Stats: statistics versus Cont (+); SE: Standard error of the mean; Cont: control (without test product); SP(−): without substance P; SP(+): in the presence of substance P.

Exposure of keratinocytes to substance P induces a substantial and statistically significant release of TNF-α. Treatment with CP96345 at 1 μM significantly reduces (90%, p<0.05) TNF-α production. This result is also very convincing: the use of this NK-1R inhibitor validates this test. The treatment of keratinocytes with the bacterial extract according to the invention allows a concentration-dependent inhibition of TNF-α release induced by substance P. The lowest tested concentration of the bacterial extract according to the invention inhibits the release of TNF-α by 60%. Although this inhibition does not reach the threshold of significance, the demonstrated concentration-response effect clearly shows that the bacterial extract according to the invention is very active on this test. At a concentration of 16.36 μg/ml protein, this inhibition is statistically significant (77% inhibition p<0.01).

Thus, the inventors demonstrate that a bacterial extract according to the invention is capable of significantly inhibiting the production of cytokines produced via substance P; this bacterial extract according to the invention is therefore effective in the treatment of cutaneous neurogenic inflammation.

EXAMPLE 4

Effect of the Bacterial Extract According to the Invention on the Gene Expression Profile of Innate Immunity in a Model of Normal Human Epidermal Keratinocytes The barrier function of the skin also includes a defense against microorganisms. The epithelium plays an active role in innate host defenses. Cutaneous antimicrobial systems are based on, among other things, the presence of certain surface lipids and certain constituent proteins. These proteins have antimicrobial activities. Moreover, the acidification of the epidermal surface plays an important role without the cutaneous antimicrobial defense. The skin thus acts not only as a physical barrier, but also as a chemical barrier. There is also an adaptive component of innate immunity based on the inducible secretion of antimicrobial peptides. The latter play an important role as mediators of inflammation by affecting epithelial and inflammatory cells, by influencing cell proliferation and cytokine production. Their mode of action consists in rupturing the plasma membrane of infectious microbes or entering the microorganism in order to interfere with intracellular metabolism. The antimicrobial peptides most studied in the skin are β-defensins and cathelicidins. Human β-defensins are the major class of antimicrobial peptides found in human epithelia and four of them have been identified in the skin, HBD 1-4. Although they belong to the same family, they are regulated by different pathways. Human β-defensin 2 (hBD2), a 4 kDa heparin-binding peptide, is one of the main cutaneous antimicrobial peptides. The expression of hBD2 peptides is inducible either by the secretion of cytokines (IL-1α and IL-1β and TNF-α) reflecting an inflammatory state, or by contact with a bacterium or fungus.

The purpose of this study is to evaluate the effects of the bacterial extract according to the invention on the gene expression of normal human epidermal keratinocytes by an RT-PCR technique on two genes related to innate immunity.

The study is carried out on normal human epidermal keratinocytes from three donors. These cells are used at their third passage. These cells are cultured in a standard medium supplemented with epidermal growth factor (EGF), pituitary extract (PE) and gentamycin, using conventional laboratory procedures.

The bacterial extract according to the invention is tested at three concentrations: 0.4, 2 and 10 μg/ml (μg/ml protein).

At the same time, calcium chloride is tested at 1.5 mM as reference product.

The keratinocytes are seeded in 24-well plates (50,000 cells per well) and cultured for 24 hours in a culture medium. The medium is then replaced by a test medium containing or not containing (control condition, DMSO) the bacterial extract according to the invention, or calcium chloride (reference product); the cells are incubated under these conditions for 48 hours. At the end of this incubation period, the cells are washed in a buffered solution and immediately frozen at a temperature of −80° C.

The expression of markers is analyzed by the RT-qPCR method on total RNA extracted from the cells under each condition. Total RNA is extracted in each sample using the Tripure Isolation® reagent according to the supplier's instructions. The quantity and quality of RNA are evaluated by capillary electrophoresis. cDNA is synthesized by reverse transcription of total RNA in the presence of oligo(dT) and Transcriptor Reverse Transcriptase. The amount of cDNA is then adjusted before the polymerase chain reaction (PCR) step.

PCR is Performed using the LightCycler® System (Roche) According to the Supplier's Data.

The data are analyzed by the Microsoft Excel software.

Fluorescence incorporation into amplified DNA is continuously measured during PCR cycles. This results in a graphical representation between the fluorescence intensity and the number of PCR cycles of a relative expression value for each marker.

The PCR technique used in this study includes two reference genes (RPL13A and TBP); these genes are used for data normalization since their expression is constitutive and therefore theoretically stable. Consequently, the expression level of the target genes is compared with the mean expression level of these two reference markers for all conditions.

The parameter RQ (relative quantification) is defined as the relative expression/100. All results are expressed in multiplicative factor, which represents the number of times the gene is overexpressed if RQ>1 or underexpressed if RQ<1.

Table 3 below Classifies the Effects of the Treated vs. Control Conditions

| Classification of effects | Multiplication factor (CF) |
| --- | --- |
| Strong stimulation | CF > 3 |
| Stimulation | 3 > CF > 2 |
| Mild stimulation, to be confirmed | 2 > CF > 1.5 |
| — | 1.5 > CF > −1.5 |
| Mild inhibition, to be confirmed | −1.5 > CF > −2 |
| Inhibition | −2 > CF > −3 |
| Strong inhibition | −3 > CF |
| No expression | Number of cycles > 33 |

The statistical analysis is carried out by an intergroup comparison by an unpaired Student's test.

Results

Treatment of normal human epidermal keratinocytes with 1.5 mM calcium chloride used as positive control induces strong expression of targeted genes in innate immunity: this result validates the experimental conditions (Table 4).

| | | Calcium chloride (1.5 mM) | | |
| --- | --- | --- | --- | --- |
| | genes | Mean | Standard deviation | SEM |
| Innate immunity | HBD2 | 5.8 | 6.1 | 3.5 |
| AMP | S100A7 | 4.1 | 3.8 | 2.2 |

AMP: antimicrobial peptides

Table 5 summarizes the effects of the bacterial extract according to the invention at the three concentrations tested

| | genes | Mean | Standard deviation | SEM |
| --- | --- | --- | --- | --- |
| | | Bacterial extract (0.2 μg/ml) | | |
| Innate immunity | HBD2 | 4.5 | 3.16 | 1.83 |
| AMP | S100A7 | 2.1 | 0.39 | 0.23 |
| | | Bacterial extract (1.0 μg/ml) | | |
| Innate immunity | HBD2 | 21.0 | 12.29 | 7.10 |
| AMP | S100A7 | 3.9 | 1.61 | 0.93 |
| | | Bacterial extract (5.0 μg/ml) | | |
| Innate immunity | HBD2 | 596.4 | 546.48 | 315.51 |
| AMP | S100A7 | 10.6 | 6.56 | 2.05 |

AMP: antimicrobial peptides

The inventors demonstrate that all tested concentrations of the bacterial extract according to the invention induce the expression of the HBD2 and S100A7 genes in a concentration-dependent manner.

The bacterial extract according to the invention has the ability to increase the induction of antimicrobial peptides. By stimulating innate immunity, antimicrobial peptides induce skin defense and help protect the skin barrier.

All these results, i.e. a reduction in cutaneous neurogenic inflammation combined with an aid to protect the skin barrier, show that the bacterial extract according to the invention genuinely acts on sensitive and/or intolerant skin.

The invention claimed is:

1. Bacterial extract of a non-pathogenic Gram-negative bacterium belonging to the class Betaproteobacteria, subfamily Neisseriaceae, comprising a 16S rRNA comprising sequence SEQ ID NO: 1, or any sequence having at least 80% identity with sequence SEQ ID NO: 1, said bacterial extract being obtained by a process consisting of the steps of:
   a. culture of said bacterium in a suitable medium to obtain a bacterial culture;
   b. liquid phase/solid phase separation of said bacterial culture and removal of the liquid phase;
   c. cell lysis of the solid phase,
   d. resuspension of the lysed solid phase in an aqueous liquid phase, wherein the aqueous liquid phase is a basic buffer comprising at least one of Tris buffer, arginine buffer and Tris-arginine buffer,
   e. liquid phase/solid phase separation and recovery of the liquid phase, wherein the liquid phase comprises the soluble cytoplasmic intracellular compounds of the bacteria,
   f. optional filtration of the liquid phase.

2. Bacterial extract according to claim 1, wherein the bacterium comprises at least one plasmid comprising sequence SEQ ID NO: 2, or any sequence having at least 80% identity with sequence SEQ ID NO: 2.

3. Bacterial extract according to claim 1, wherein the bacterium is LMB64, deposited at the CNCM on 8 Apr. 2010 under number I-4290.

4. A method for treating cutaneous neurogenic inflammation in a person in need thereof, comprising the administration of a bacterial extract according to claim 1.

5. The method according to claim 4, wherein the cutaneous neurogenic inflammation includes sensitive skin and/or intolerant skin.

6. Cosmetic or dermatological composition comprising a bacterial extract according to claim 1 and at least one cosmetically or dermatologically acceptable excipient.

7. Cosmetic or dermatological composition according to claim 6, herein the cosmetic or dermatological composition is suitable for topical application.

8. A method for treating cutaneous neurogenic inflammation in a subject in need thereof comprising the administration of a dermatological composition according to claim 6.

9. Method according to claim 8, wherein the cutaneous neurogenic inflammation includes sensitive skin and/or intolerant skin.

* * * * *